US008894835B2

(12) United States Patent
Hartmann et al.

(10) Patent No.: US 8,894,835 B2
(45) Date of Patent: Nov. 25, 2014

(54) METHOD OF INSPECTING A METAL COATING AND A METHOD FOR ANALYTICAL CONTROL OF A DEPOSITION ELECTROLYTE SERVING TO DEPOSIT SAID METAL COATING

(75) Inventors: Philip Hartmann, Berlin (DE); Michael Jonat, Falkensee (DE); Mathias Wuensche, Panketal (DE)

(73) Assignee: Atotech Deutschland GmbH (DE)

( * ) Notice: Subject to any disclaimer, the term of this patent is extended or adjusted under 35 U.S.C. 154(b) by 843 days.

(21) Appl. No.: 13/127,507

(22) PCT Filed: Oct. 26, 2009

(86) PCT No.: PCT/EP2009/007741
§ 371 (c)(1),
(2), (4) Date: May 4, 2011

(87) PCT Pub. No.: WO2010/051937
PCT Pub. Date: May 14, 2010

(65) Prior Publication Data
US 2011/0215003 A1    Sep. 8, 2011

(30) Foreign Application Priority Data

Nov. 5, 2008  (DE) .......................... 10 2008 056 470

(51) Int. Cl.
*C25D 21/12*   (2006.01)
*G01N 27/42*   (2006.01)
*C25D 5/18*    (2006.01)

(52) U.S. Cl.
CPC .............. *G01N 27/42* (2013.01); *C25D 21/12* (2013.01); *C25D 5/18* (2013.01)
USPC .............................. 205/81; 205/223; 205/791

(58) Field of Classification Search
USPC ........................................................... 205/81
See application file for complete search history.

(56) References Cited

U.S. PATENT DOCUMENTS 4,132,605 A * 1/1979 Tench et al. .................... 205/787
4,294,667 A   10/1981 Yamamoto et al.

(Continued)

FOREIGN PATENT DOCUMENTS

DE      3010750 C2    1/1990
EP      0760473 A1    5/1997
TW      098 136 471   11/2008

OTHER PUBLICATIONS

M. Hap et al., DUR-Ni® 4000—"Verbesserter, Korrosionsschutz mit verbesserter Prozesssicherheit", Galvanotechnik, 4 (2004), pp. 894-897. Relevance is that it was cited on p. 2 of the instant application.

(Continued)

Primary Examiner — Bryan D. Ripa
(74) Attorney, Agent, or Firm — Paul & Paul

(57) ABSTRACT

For fast and secure determination of the quality of a metal coating as well as of an electrolyte for depositing a metal, in particular for electrolytic deposition of nickel such as of semi-gloss nickel and bright nickel and for analytical control of the deposition electrolyte, a method of inspecting a metal coating is provided, which involves the following method steps: a) depositing the metal coating from a deposition electrolyte onto a working electrode; b) electrolytically dissolving the metal coating through anodic polarization of the working electrode with respect to a counter electrode, which is in electrolytic contact with the working electrode; c) recording an electrical dissolution potential at the working electrode over time, said potential occurring during a dissolution of the metal coating; and d) determining a time-averaged vale of the dissolution potential.

10 Claims, 5 Drawing Sheets

(56) References Cited

U.S. PATENT DOCUMENTS

Figure 1:
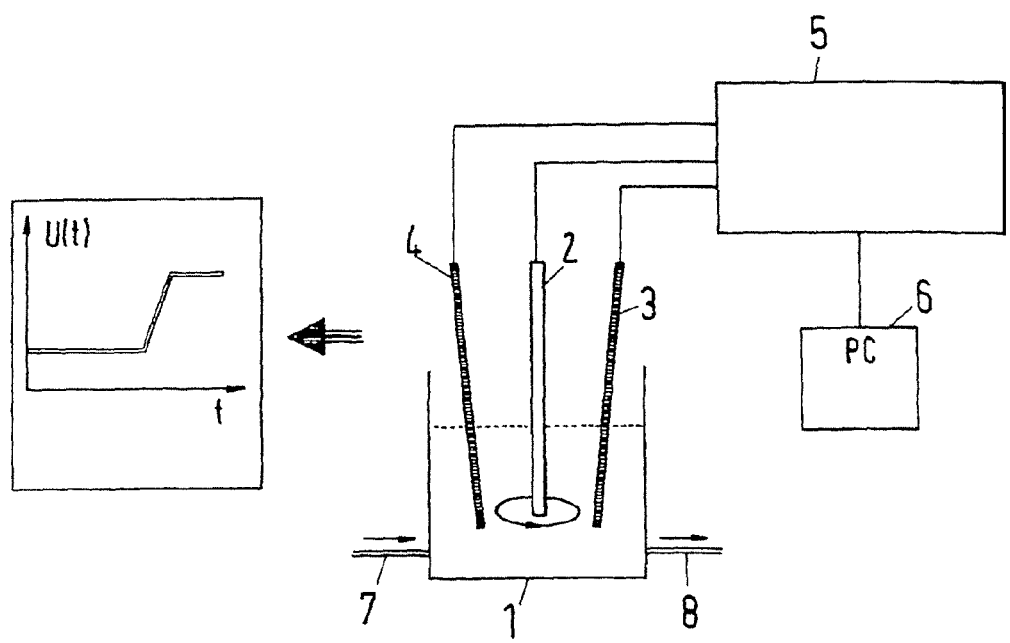

| | | | |
|---|---|---|---|
| 4,479,852 A * | 10/1984 | Bindra et al. ................... 205/81 |
| 5,523,182 A | 6/1996 | Ovshinsky et al. |
| 6,592,737 B1 | 7/2003 | Robertson |
| 6,808,611 B2 * | 10/2004 | Sun et al. ........................ 205/81 |
| 6,899,805 B2 * | 5/2005 | Chen et al. .................... 205/794 |
| 7,384,535 B2 * | 6/2008 | Sonnenberg et al. .......... 205/775 |
| 2004/0108214 A1 * | 6/2004 | Robertson ....................... 205/83 |

OTHER PUBLICATIONS

STEP: "Simultaneous Thickness and Electrode Potential Determination"; Din 50022, Berlin, Germany, pp. 1-12. Relevance is that it was cited on p. 2 of the instant application.

Besseyrias et al., "A Study of Galvanic Corrosion During Coulometric Dissolution of Galvannealed Steel", Corrosion science, oxford, GB, vol. 37, No. 4, Apr. 1, 1995 Seiten pp. 587-595. Relevance is that this was cited as a category "X" in the International Search Report.

Swathirajan et al, "Electrodeposition of Zinc+Nickel Alloy Phases and Electrochemical Stripping Studies of the Anomalous Codeposition of Inc", Journal of electroanalytical chemistry and interfacialelectro chemistry, Elsevier, Amsterdam, NL, vol. 221, No. 1-2, 24. April, 2987 (Apr. 24, 1987), Seiten, pp. 211-228. Relevance is that it was cited as a category "X" in the International Search Report.

"Standard Test Method for Simultaneous Thickness and Electrode Potential determination of Individual Layers in Multilayer Nickel Deposit (STEP Test)" ASTM Standard B764, (Apr. 4, 2004) pp. 509-514, XP 009127826. Relevance is that it was cited as a category "X" in the International Search Report.

Harbulak Edward P: "Simultaneous Thickness and Electrochemicalpotential Determination of Individual Layers in in Multilayer Nickel Deposits" Plating and Surface Finishing American Electroplaters Societ, Inc. East Orange, US, vol. 67, No. 2 Jan. 2, 1980, pp. 49-54, XP008117867. Relevance is that it was cited as a category "X" in the International Search Report.

M. Gugau and Bedburg, "Corrosion at material composites having metallic coatings, functional components"; Published by Technical University of Darmstadt with alleged but unproven date of Apr. 14, 2000; Alledgedly Published in Germany.

M. Sorg and TH. Ladwein, "Electrochemical characterization of electroless nickel coatings". Published in a lecture in a conference in Bonn, Germany allegedly in 2006.

TH. Ladwein and M. Sorg, "Electrochemical characterization of electroless nickel coatings". Published as a conference paper during a lecture held at Bonn, Germany allegedly in 2006; by Chemische Metallabscheldung in Bonn, Germany.

M. Sorg and TH. Ladwein, "Electrochemical characterization of electroless nickel coatings", all edged to have been published at the lecture in Bonn, Germany as a conference paper in 2006, by Hochschule fur Wirtschaft und Technik Aalen.

E. Schmeling, "Properties and assessment of electroless plated nickel", Metalloberflache, Published by Carl Hanser Verlag, in Munich, Germany, in 1987; pp. 353-358.

D. Milanova and G. Gawrilov, "Anodic behavior of alloyed electroless nickel coatings having low phosphorus content", Publisher Metallwissenscahft und Technik in 1998, in Germany; pp. 361-364.

J. Weber and R. Waser, "Comparative corrosions studies on chemical and galvanic nickel deposits", Published by J. Weber and R. Waser, Oberilade-Surface in1985; pp. 173-179.

Heinz-Gunther Schenzel, "Micro-structure and corrosion behavior of chemical nickel-phosphorus coatings", Published in 1990 by VDI-Verlag, GmbH, in Dusseldorf Germany in 1990; pp. IV-IX, 1-141.

Waldenmar. Immel, "Structure related behavior of nickel/phosphorus coatings in various attacking media", Alledgedly Published by Dr. Waldenmar Immel, in Solingen, Germany; Date Uncertain, but it references the 1970's; pp. 241-246 (Also pp. 118-123 in alternate numbering.

Heinz-Gunther Schenzel, "Micro structure and corrosion behavior of chemical nickel-phosphorus coatings", Alledgedly Published by VDI VERLAG, 1990, in Dusseldorf Germany; pp. 128-131.

Prof. Dr. Habil Nasser Kanani, "Chemical nickel plating", Published by Schriftenreihe Galvanotechnik Und Oberflachenbehandlug in 2007 in Bad Saulgau Germany; pp. 362-402.

* cited by examiner

METHOD OF INSPECTING A METAL COATING AND A METHOD FOR ANALYTICAL CONTROL OF A DEPOSITION ELECTROLYTE SERVING TO DEPOSIT SAID METAL COATING

FIELD OF THE INVENTION

The present invention relates to a method of inspecting a metal coating which is either located alone on a substrate or which is a constituent part of a multi-layered metal coating system, as well as to a method of analytical control of a deposition electrolyte serving to deposit such a metal coating.

PRIOR ART

In order to protect metals from corrosion, it has been found advantageous to deposit a multiple nickel coating system on the surfaces thereof. Parts made from copper, brass or steel but also parts made from plastic material can be coated with this coating system for example. Typically, a thin coating of chromium is additionally deposited onto said multiple nickel coating system. The nickel coating serves for decorative purposes and also to protect the base material from corrosion.

The multiple nickel coating system usually consists of a quite thick base layer made from semi gloss nickel. Its thickness may be 10-20 µm for example. Sulphur-free additives are utilized for depositing it. A thinner bright nickel coating or a matte nickel coating of a typical thickness of 5-15 µm is deposited onto this base coating, using sulphur-containing additives. Alternatively, a bright nickel coating with a very high sulphur content may first be deposited onto the semi-gloss nickel coating and thereon the above mentioned bright or matte nickel coating. An even thinner semi-gloss nickel coating is in turn deposited onto the bright or matte nickel coating, said thinner semi-gloss coating being deposited using organic additives and being for example 1-3 µm thick. This nickel coating may additionally contain fine inorganic particles which are incorporated during deposition. A very thin chromium layer of only 0.2-0.4 µm thick is then generally deposited onto said thin semi-gloss nickel coating. If the top semi-gloss nickel coating contains particles, pores, form in the chromium coating since no chromium can be deposited where there are particles located superficially in the nickel coating.

The corrosion protection of this coating system relies on the principle that the discrete nickel coatings comprise different dissolution potentials so that they behave in different ways with respect to corrosion: the bright or matte nickel coating has a dissolution potential that is more negative that that of the two semi-gloss coatings. Compared to the bright or matte nickel coating, the sulphur-rich coating, which may be deposited optionally, is even less noble. The lower semi-gloss nickel coating has a more positive potential than the top semi-gloss nickel layer, which possibly contains particles. As a result, one obtains an active protection against corrosion: the corrosion may encroach through the pores contained in the chromium coating and reach the upper semi-gloss nickel coating and there beneath the bright or matte and possibly even less noble sulphur-rich bright nickel coating. Since corrosion occurs uniformly through the pores of the chromium coating in the nickel coating underneath and not unevenly, for example through pitting, the surface of the protected component parts remains visually intact for a long period of time. The non-noble bright or matte nickel coating and possibly also the sulphur-rich nickel coating may thereby sacrifice themselves (M. Häp et al., "DUR-Ni®4000—Verbesserter Korrosionsschutz mit verbesserter Prozesssicherheit [Improved Corrosion Protection with Improved Process Safety]", Galvanotechnik, 4 (2004) 894-897).

In order to verify the quality of the deposited nickel coating system, the CASS test (CASS: Copper Accelerated Salt Spray) can be utilized. With this testing method, the parts to be evaluated are placed into a salt spray chamber in which a sprayed salt solution, in the event of the CASS test a solution of copper chloride and acetic acid, corrodes the parts. Testing of the parts is very long though so that it takes a considerable amount of time before it can be seen whether the manufactured parts meet the requirements.

For this reason, other methods have been developed, so for example the Dubpernell Test which allows for determining the number of pores in the chromium coating as the measure for the corrosion resistance of the protected surfaces (M. Häp et al., ibid.).

Another method to verify the quality of the deposited nickel coating system is the STEP test (STEP: Simultaneous Thickness and Electrode Potential Determination; DIN 50022). The method disclosed in DIN 50022 comprises the following method steps: electrolytic dissolution of a metal coating deposited on a work piece by anodic polarization of the work piece being used as a working electrode with respect to a counter electrode which is in electrolytic contact (via a dissolution electrolyte) with a counter electrode; and recording a potential during dissolution of the metal coating at the working electrode over time. With this STEP test, the parameters which are relevant for the evolution of corrosion, namely the coating thicknesses of the individual nickel coatings as well as the differences in their potentials can be measured in one single method step. Using this method, one takes advantage of the fact that the electric potential measured against a reference electrode during stripping changes in leaps and bounds after stripping of a nickel coating. This occurs after the respective nickel coatings have dissolved, the measured dissolution potentials depending i.a. on the nature of the respective nickel coating. The potential difference between the bright or the matte nickel coating and the lower semi-gloss nickel coating should range from 120 through 140 mV whilst the potential difference between the bright or the matte nickel coating and the top semi-gloss nickel coating, which may moreover contain particles, should range from 20 through 50 mV. The potential difference between the sulphur-rich and the bright or matte nickel coating should range from 15 through 25 mV. The bright or matte nickel coating is less noble than the semi-gloss base coating and also less noble than the top semi-gloss nickel coating, which may moreover contain particles, whilst being nobler than the sulphur-rich nickel coating. To carry out the STEP test, the coating combination to be inspected, which is located on a coated part coming from production, is anodically deplated. Referring to the experimental conditions and to the experimental structure, the reader is referred to DIN 50022.

Moreover a method of inspecting the effect of corrosion protection of a coating having a high protection resistance is known from DE 30 10 750 C2. This method comprises the following method steps: depositing the protection coating onto a metal plate and locating the coated metal plate, a reference electrode and a counter electrode in a corroding medium; determining a potential spontaneously arising and electrolyzing the coated metal plate at said potential; polarizing the metal plate by impulse polarization etc. in order to determine whether the coated metal plate shows damaging or not; and determining a very small current/voltage change or determining an anodic and/or cathodic polarization curve.

PROBLEM AND OBJECT OF THE INVENTION

It has been found out that even the STEP test is not safe and fast enough to be able to meet all the needs for mass production with high quality requirements. The duration of an inspection inclusive of the manufacturing of the samples needed for inspection generally is of at least 90 min. Within this period of time, many coated parts of unsatisfactory quality may be manufactured in a mass-production factory without any possibility of finding this out before. In the worst case, these parts must be eliminated. This is not acceptable. Moreover, it has been found out that the values of the potential difference determined with the STEP test are subject to quite strong fluctuations so that the statement regarding the quality of the parts manufactured is not sufficiently reliable. Finally, it is not possible to draw individual deductions regarding the causes of possible differences from given reference values because the values obtained with the STEP test are determined by the respective quality of two neighbouring coatings.

Accordingly, it is the object of the present invention to find a method by means of which a fast, secure and, as a result thereof, reliable evaluation of the quality of a deposited layer of metal is made possible, said metal coating being either deposited alone onto a substrate or being a component part of a multilayered metal coating system. Moreover, it aims at allowing to control the deposition electrolyte used for depositing the metal coating in such a manner that the metal coatings deposited therewith have the desired quality. Finally, it aims at making it possible to directly draw deductions as to the monitoring and guiding of the deposition electrolyte in order to permit to keep the quality of the deposited coatings constant more easily.

DESCRIPTION OF THE INVENTION

The object is achieved by the method of inspecting a metal coating as set forth in patent claim 1 and by the method of analytical control of a deposition electrolyte serving to deposit said metal coating. Preferred embodiments of the invention are recited in the dependent claims.

The methods of the invention can be used for monitoring the quality of deposited coatings of any metal and of the deposition electrolytes used for this purpose. Nickel, copper, tin, zinc, lead, cadmium, chromium, iron, cobalt, silver, gold, platinum, palladium, rhodium as well as the alloys thereof are mentioned by way of example. The methods rely on the principle that a metal coating is deposited from the deposition electrolyte to be inspected and under the deposition conditions which are important for deposition, the quality of the metal coating being determined by the deposition conditions as well as by the composition of the deposition electrolyte and that this quality is determined by measuring the dissolution potential of the metal coating deposited. Accordingly, the dissolution potential is authoritative for the deposition conditions to be observed and for the composition of the deposition electrolyte. The dissolution potential however is not affected by all the parameters of the deposition conditions and by all the components of the deposition electrolyte to the same extent. The dissolution potential is mainly indicative of the corrosion resistance of the deposited metal coating and is, as a result thereof, a measurement parameter for determining those parameters of the deposition conditions as well as those components of the deposition electrolyte which have decisive influence over the corrosion resistance of the deposited metal coating.

The method of the invention for inspecting the metal coating involves the following method steps:
  a) depositing the metal coating from the deposition electrolyte onto a working electrode;
  b) electrolytically dissolving the metal coating through anodic polarisation of the working electrode with respect to a counter electrode, which is in electrolytic contact with the working electrode;
  c) recording an electrical dissolution potential at the working electrode over time, said potential occurring during dissolution of the metal coating; and
  d) determining a time-averaged value of the dissolution potential.

In order to be capable of determining the quality of the deposited metal coating relative to other metal coatings, the method optionally comprises, after method step d), the additional method step e):
  e) comparing the time-averaged value of the dissolution potential with a reference value.

The method of the invention for analytical control of the deposition electrolyte serving for depositing the metal coating involves the following method steps:
  a) depositing the metal coating from the deposition electrolyte onto a working electrode;
  b) electrolytically dissolving the metal coating through anodic polarisation of the working electrode with respect to a counter electrode, which is in electrolytic contact with the working electrode;
  c) recording an electrical dissolution potential at the working electrode over time, said potential occurring during dissolution of the metal coating;
  d) determining a time-averaged value of the dissolution potential;
  e) determining a difference between the time-averaged value of the dissolution potential and a reference value; and
  f) allocating said difference to a difference between the concentration of a component of the deposition electrolyte determining the dissolution potential and its reference concentration.

The metal coating can in particular be a constituent part of a multilayered metal coating system. As a result, several metal coatings can be deposited one after the other onto the working electrode and then be dissolved again one after the other. For each metal coating, the electric potential at the working electrode is thereby recorded separately over time and then a time-averaged value of the dissolution potential is respectively determined for each metal coating in the metal coating system.

According to method step a), the metal coating is at first deposited from the deposition electrolyte in both methods of the invention. The deposition electrolyte is the solution which is used for manufacturing the metal-plated parts in production. Moreover, those deposition conditions are preferably chosen, which are used for depositing the metal coating onto the parts serving for production. It is preferred to thereby take into consideration the fact that the parts used in production have in most cases complex shapes and that the current density can vary at different places on one and the same part during deposition. Since, accordingly, the corrodibility may also vary at the different places, a preferably corrodible place may for example be examined and the local current density corresponding to this place may be set in accordance with the invention during deposition, also in method step a). In the alternative, parameter values may also be selected for the deposition conditions, which differ from those set during production. In the last case, the deposition conditions during deposition of the metal coating onto the working electrode should be selected and fixed in order to obtain comparable conditions for different measurements.

The working electrode preferably consists of an inert metal on which the metal can be readily deposited, more specifically in a reproducible and repeatable manner. This is the reason why platinum is the preferred material of choice for the working electrode. After deposition and renewed dissolution of the metal coating, platinum can be pre-treated for renewed metal deposition with an appropriate treatment so that this metal deposition can be reproduced and take place like the previous one. Such a conditioning may for example be performed by bringing the platinum electrode into contact with a diluted sulphuric acid solution and through anodic polarisation of the platinum electrode according to an imposed potential-time relationship. This is also a reason why platinum is to be preferred over other metals for the working electrode. A rotating disc electrode such as a rotating platinum electrode is preferred since it permits to set constant and reproducible hydrodynamic conditions at the working electrode. As the rotating disc electrode, the rotating platinum electrode is typically utilized in a form in which a platinum disc of for example 3 mm in diameter is embedded in an end side of a cylinder made from an electrically isolating material, the surface of the disc being flush with the end side of the cylinder. For rotation, the cylinder is caused to rotate about its axis, for example with 200-2000 revolutions per minute (rpm), preferably with about 500 rpm.

The working electrode and the counter electrode as well as, at need, other electrodes such as a reference electrode are preferably accommodated in a measurement cell that is separated from the tank in which the parts serving for production are metal coated. Preferably, the deposition electrolyte originates from the coating tank and is continuously conveyed from said tank toward the working electrode. For this purpose, appropriate pipe or hose lines can be provided for circulating the deposition electrolyte between the coating tank and the measurement cell. The measurement cell can be heatable in case metal needs to be deposited at an increased temperature.

According to measurement step b), the metal coating deposited on the working electrode is next electrolytically dissolved again in the two methods of the invention by anodically polarising the working electrode with respect to a counter electrode which is in electrolytic contact with said working electrode. This means that the working electrode and the counter electrode are brought together into contact with a dissolution electrolyte. Like the working electrode, the counter electrode can in particular also consist of platinum in order to make certain that they can be used repeatedly. Between the working electrode and the counter electrode a voltage is preferably applied in such a manner that a constant current permanently flows between these two electrodes for the purpose of anodic dissolution of the metal coating deposited thereon. Such a polarisation of the working electrode is also referred to as a galvanostatic condition. An electric circuit is used for this purpose through which an electric voltage is applied between the working electrode and the counter electrode in such a manner that a constant current flows between the two electrodes. This dissolution current can be set quite high in order to allow for fast measurement. A current density of 5 through 50 $A/dm^2$, preferably of 10 through 30 $A/dm^2$, can be chosen. The selected current density during dissolution depends i.a. on the thickness of the metal coating to be dissolved for a very thin metal coating should be deplated with a low dissolution current in order to allow for showing a potential plateau that will be able to be resolved in terms of time. Moreover, the metal coatings to be dissolved can also form passivation layers, even at varying dissolution current densities, i.e., varying dissolution potentials, so that the dissolution is impeded. For this reason, it may even be necessary for measurement to consecutively set different current density values when metal coatings forming passive layers at different potentials are deplated one after the other in a multilayered metal coating system. The potential at the working electrode is then measured with respect to a third electrode, which is configured to be the reference electrode. The arrangement of the three electrodes is usually referred to as a three-electrode arrangement. The voltage building up between the working electrode and the reference electrode is measured if possible without current, i.e., the current flowing between these two electrodes is minimized. The reference electrode is preferably an electrode that adopts a constant electric potential and that is configured to be a metal electrode for example for this purpose, said metal electrode being in equilibrium with a hardly soluble salt of this metal such as a silver/silver chloride electrode.

The deposited metal coating is preferably anodically dissolved in a special dissolution electrolyte. The dissolution electrolyte in particular contains ions of the metal to be deposited as well as at least one acid. Preferably, the composition of the dissolution electrolyte differs from the composition of the deposition electrolyte. The dissolution electrolyte should in particular contain no additive affecting the quality of the deposition such as the grain size. As a result, the working electrode provided with the metal coating is transferred into an electrolysis cell containing the dissolution electrolyte and comprising the counter electrode prior to performing the following method step b). The advantage of using the dissolution electrolyte is that the dissolution potential measured is much more constant than when using the deposition electrolyte. If the deposition electrolyte or an electrolyte also containing additives affecting the quality of the deposition is used to dissolve a metal coating deposited on the working electrode, one obtains respectively a dissolution potential that considerably differs from the dissolution potential obtained with a dissolution electrolyte that contains no such additives. Accordingly, the dissolution potential also significantly depends on the composition of the dissolution electrolyte.

Through anodic polarisation of the working electrode and the current thus preferably flowing at a constant level an electric dissolution potential settles between the working electrode and the counter electrode. Accordingly, according to method step c), one records in both methods of the invention the dissolution potential occurring during dissolution of the metal coating, said dissolution potential being determined depending on time. The dissolution potential depends both on the quality of the deposited metal coating and on the conditions at which the dissolution takes place. If constant conditions are settled during dissolution and if the quality of the metal coating is the same in each removed layer of the coating, one measures a constant dissolution potential. It is only after complete removal of the metal coating that the measured potential changes since then the surface of the working electrode or another metal coating, which is located beneath the metal coating and which is made from another material or from the same material as the deplated metal coating comes into contact with the dissolution electrolyte, wherein said other metal coating made from the same material has been deposited although under modified conditions and is also deplated then as a result thereof. In case an aqueous dissolution electrolyte is used, the potential then shifts to a value that corresponds to the oxygen formation through water decomposition when the working electrode is located underneath the depleted metal coating. Otherwise, the potential shifts to the dissolution potential of the other metal coating laid bare underneath the depleted metal coating.

To evaluate the corrosion resistance of the deposited metal coating, one then first determines, according to method step d) in both methods of the invention, from the dissolution potential that has been recorded depending on time, a time-averaged value of the dissolution potential. For this purpose, values of the dissolution potential at the working electrode are measured within an imposed time interval and these measured values are averaged. The time interval is preferably determined so as to include a (steady) plateau value for the dissolution potential so that the fluctuation of the potential is as small as possible within this time interval. The time interval can preferably be chosen constant for each measurement and may start after a starting phase has come to an end and may end before the dissolution process has been completed. If several metal coatings have been deposited one above the other on the working electrode, the dissolution potential building up over time for every single layer is recorded and then a time-averaged dissolution potential is respectively determined. The respective dissolution potentials may of course only be measured when the corresponding metal coating in a multilayered metal coating system is exposed.

In the method for inspecting the metal coating, one then compares preferably, according to method step e), the time-averaged value of the dissolution potential with a reference value or, if one multilayered metal coating system has several metal coatings, one compares the time-averaged value of each dissolution potential with a corresponding reference value corresponding to the respective metal. This comparison permits to determine the quality of the metal coating deposited. If the dissolution potential lies within an admissible tolerance range about the reference value, the quality corresponds to the requirements. Otherwise, the quality differs from the requirements. The reference value is fixed for a certain type of metal coating and is determined empirically.

In the method for analytic control of the deposition electrolyte, one determines, as an alternative thereto and according to method steps e) and f), a difference between the time-averaged value of the dissolution potential for a metal coating and the reference value (method step e) and the difference is then allocated to a difference between the concentration of a component of the deposition electrolyte determining the dissolution potential and its reference concentration (method step f). If the reference value is observed, there is no need to take measures for adjusting the deposition electrolyte as a result thereof since in this case there is no difference between the composition of the deposition electrolyte and an imposed composition. By contrast, the composition of the electrolyte must be adapted if it appears that the reference value is not observed for the dissolution potential. In this case, the concentration of a component of the deposition electrolyte determining the dissolution potential must be raised or lowered in order to reach again the reference value for the dissolution potential. In order to be capable of locating which measures must be taken to raise or lower the concentration of this component it is therefore advantageous to associate with every possible difference between the time-averaged value of the dissolution potential and the reference value a concentration difference for the component of concern of the electrolyte (and to note it in an allocation table) so that amounts to be added can for example be fixed in order to raise its concentration. This allocation table must be determined empirically by adding an additive to a deposition electrolyte until the actually expected dissolution potential is obtained if it does not correspond to the reference value. The added amount of additive corresponds to the concentration difference. Further, it may also be advantageous to determine the actual concentration of this component in the deposition electrolyte. For this purpose one may for example also elaborate an allocation table in which concentration values of the component are allocated to corresponding time-averaged values of the dissolution potential.

Generally, the components determining the dissolution potential of a metal are additives that affect the metal deposition, such as the grain size and the co-deposition of other chemical elements such as sulphur. Such a component may for example also be a mixture of different chemical substances that are respectively added all together to the deposition electrolyte.

Further, the values obtained in accordance with the invention for the dissolution potential may also be used in order to calculate the difference in the time-averaged dissolution potentials for example between two consecutive metal coatings in a multilayered metal coating system. By this subtraction, one obtains potential differences which should be identical with the potential differences obtained with the STEP test. Because of the poorer reproducibility of the measurements with the STEP test one obtains results that do not completely coincide, though.

In a preferred embodiment of the invention the metal coating is an electrolytically deposited nickel coating. As specifically discussed in the introductory portion of this specification and insofar explicitly incorporated in the disclosure scope of the present invention, electrolytically deposited nickel coatings are deposited as corrosion protective coatings on parts made from different materials such as copper, brass or steel or also plastic material, the nickel coatings being deposited in different qualities and in a certain sequence, namely for example as a semi-gloss nickel coating, a bright nickel coating, at need with an intermediate layer particularly rich in sulphur, and again as a semi-gloss nickel coating, which is at need deposited together with particles. The basic composition of a nickel deposition electrolyte is typically what is referred to as a Watts nickel bath, which contains nickel ions, chloride ions, sulphate ions and boric acid, for example in the following composition: 60 g/l $NiCl_2.6H_2O$, 270 g/l $NiSO_4.6H_2O$, 45 g/l $H_3BO_3$. The pH value of the deposition electrolyte generally ranges from 2.5 through 6.0, preferably from 3 through 4.5, and is more specifically about 4.0. Deposition occurs at a temperature of 40-70° C., preferably of 50-60° C. and in particular at a temperature of 55° C. The respective coatings are electrolytically deposited from deposition electrolytes of different compositions, in particular with regards to the additives. The semi-gloss base coating on the substrate material typically contains salicylic acid, ethyne derivatives such as hexyne diol or butyne diol, propargyl alcohol derivatives, formaldehyde and/or chloral hydrate or also mixtures of these compounds as additives. The possibly deposited sulphur-rich bright or matte intermediate layer typically contains saccharine, sulphonic acids and/or ethyne derivatives as additives. The bright nickel coating typically contains as additives sulphur-containing compounds such as toluene sulfonic acid or propargyl sulfonates and additionally saccharine instead of salicylic acid or mixtures of these compounds. The upper semi-gloss nickel coating typically contains saccharine or a saccharine salt, chloral hydrate and/or formaldehyde or also mixtures of these compounds as additives and possibly additionally particles of $SiO_2$, $Al_2O_3$ for example. Moreover, the deposition electrolytes may contain other additives such as brighteners and surfactants.

If the metal coating to be inspected is a nickel coating or if the deposition electrolyte to be inspected serves for depositing a nickel coating, one may also use a nickel ion containing solution as the dissolution electrolyte. For anodic dissolution of a nickel coating, one preferably uses a dissolution electrolyte that contains nickel chloride, sodium chloride and boric acid, preferably in the following composition: 300 g/l $NiCl_2.6H_2O$, 50 g/l NaCl, 25 g/l $H_3BO_3$. The preferred pH of this electrolyte is 3.0. The dissolution process is preferably performed at room temperature.

The methods of the invention may be operated both as what are referred to as At Line methods and as so-called online methods. In the At Line method, a sample of the deposition electrolyte is taken manually from a production tank and is brought to a measurement equipment in a laboratory. There, the necessary tests are made. With the online method, the deposition electrolyte is automatically tapped from the production tank and transferred to the measurement equipment. In this case, the deposition electrolyte can be tapped in short intervals so that the respective measurements occur in short succession.

For the online method, the measurement cell with the rotating platinum electrode, with the counter electrode and with the reference electrode is hydraulically brought into contact with the deposition tank for the deposition electrolyte in which to be metallized parts are produced. Before performing the methods of the invention, the platinum electrode is preferably cleaned and then conditioned in order to prepare it for measurement. For this purpose, it is preferred to flush a diluted sulphuric acid solution into the measurement cell. Next, the platinum electrode is anodically and cathodically polarized according to a predetermined programme. Next, the deposition electrolyte for carrying out method step a) is flushed from the deposition tank into the measurement cell. After that, metal is deposited onto the platinum electrode. Next, the deposition electrolyte is removed from the measurement cell and is replaced by the dissolution electrolyte after rinsing with water for example. After that, one performs the method steps of the invention in order to determine the dissolution potential of the deposited metal coating on the platinum electrode. Upon completion of the measurements, the dissolution electrolyte is removed again from the measurement cell. After the measurement cell has been possibly rinsed, the platinum electrode is conditioned again. This method can be performed repeatedly for a deposition electrolyte. If the production line has several metal baths with different compositions for the parts to be coated, one may provide either several such measurement cells or one measurement cell is alternately filled with the respective deposition electrolyte so that the results obtained in the measurement cell during measurement are obtained alternately for the different deposition electrolytes. Alternatively, the different metal coatings may at first be deposited one after the other on the working electrode and then be deplated again successively. One determines a time-averaged dissolution potential for each metal coated that is being deplated.

The respectively determined potential values are processed with appropriate means in order to calculate from the measured time-dependent values of the potential the time-averaged values for the dissolution potential and in order to make a comparison between a time-averaged value for the dissolution potential and a reference value. In the same way, these means also serve to determine the difference between the time-averaged value of the dissolution potential and a reference value and to allocate the difference to a difference between the concentration of a component of the deposition electrolyte determining the dissolution potential and its nominal concentration. At need, one also calculates with these means the difference of the potential values determined for consecutive or non consecutive metal coatings in a multilayered metal coating system. Such type means can be accordingly programmed process computers. Moreover, these means may serve for documentation and for statistical evaluation. Finally, these means may also serve for controlling the measurement cell and the apparatus for supplying the measurement cell with solutions such as with the deposition electrolyte, with the dissolution electrolyte, with flush water and with a solution for conditioning the platinum electrode so that the methods of the invention can be performed in automated fashion as online methods.

With the methods of the invention it is possible for the first time to react within quite short a time to changes in the quality of deposited metal coatings that are deposited alone on a substrate or that are located in a multilayered metal coating system with regards to their corrosion resistance: Whilst it was possible to obtain a qualified statement about the corrosion resistance of coatings or of coating systems within about 90 min with the conventional methods, the methods of the invention now permit to locate after already 20-30 min whether the deposition conditions or the composition of the respective deposition electrolyte correspond to the requirements. Further, the methods of the invention make it possible to draw direct deductions as to the composition of one individual deposition electrolyte. This is not possible with the STEP test because the measurement values obtained therewith only yield information about the quality of two neighbouring metal coatings together. Finally, it has been found out that the methods of the invention yield more precise, i.e., more reproducible results than the STEP test. For using the STEP test one has to reckon with a greater standard deviation than with the method of the invention. This may be due to the fact that the potential difference values determined with this method depend i.a. on the kind of the parts taken from production and on which the metal coatings have been deposited as well as on the place on a part at which the measurement has been performed.

Finally, the method of the invention for inspecting a metal coating, which involves the method steps a) through d), makes it possible to determine the potential differences between consecutive metal coatings in a multilayered system such as a multiple nickel coating system. Alternatively, a potential difference for consecutive coatings made from different metals such as from nickel and chromium may of course also be determined. For this purpose, the time-averaged values of the dissolution potentials of the consecutive layers, which have been deposited individually on the working electrode, and then the potential difference there between are determined by subtraction.

Further, it is also possible to determine from the time dependence of the dissolution potential for a metal coating the coating thickness thereof and, taking into consideration the deposition current, the current yield during deposition.

Figure 2:
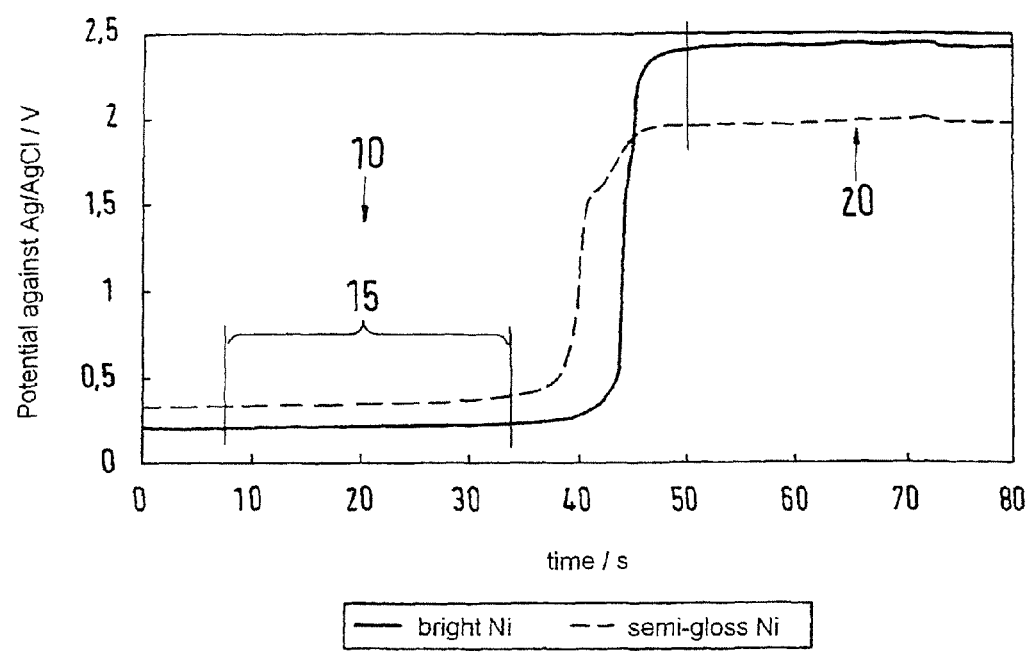
Figure 3:
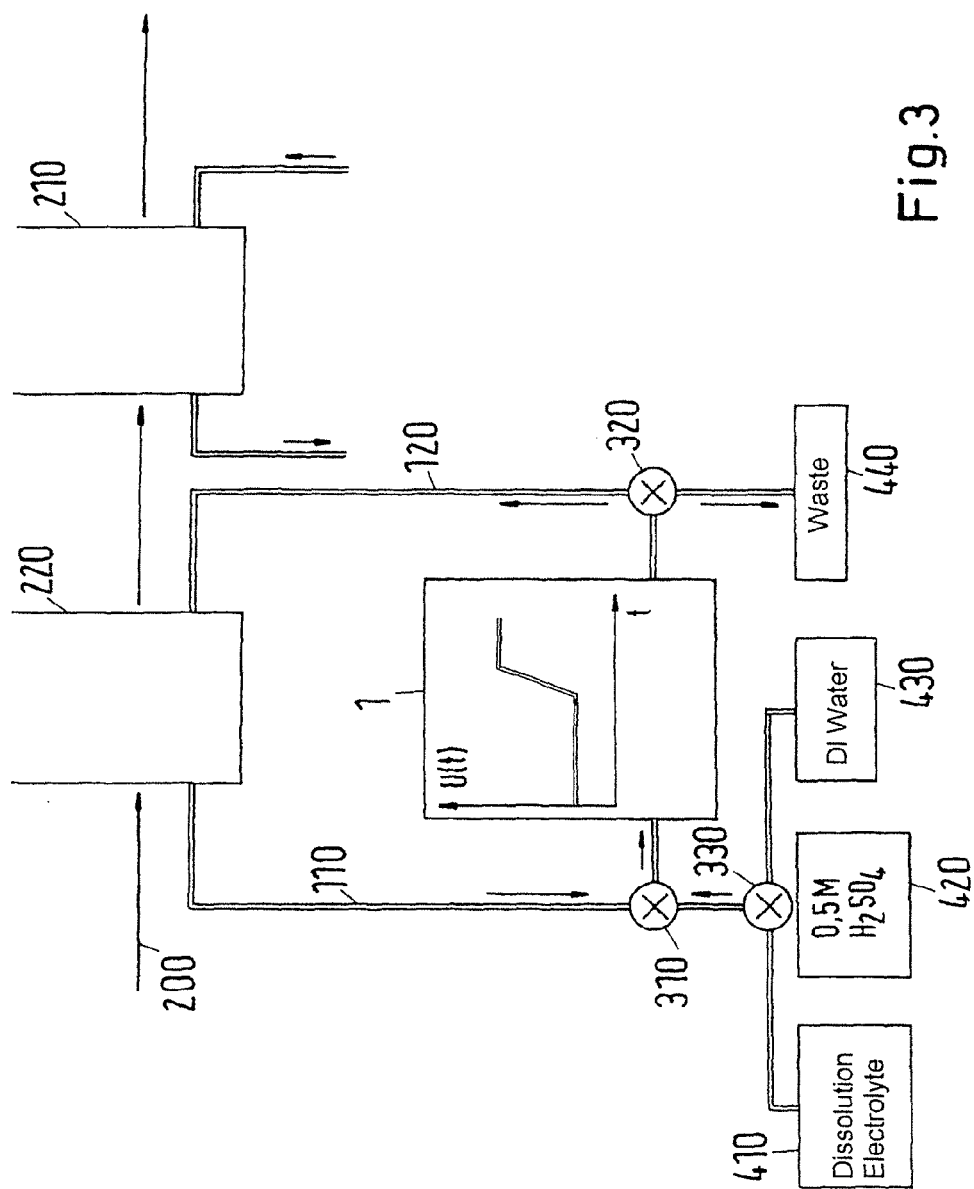
Figure 4:
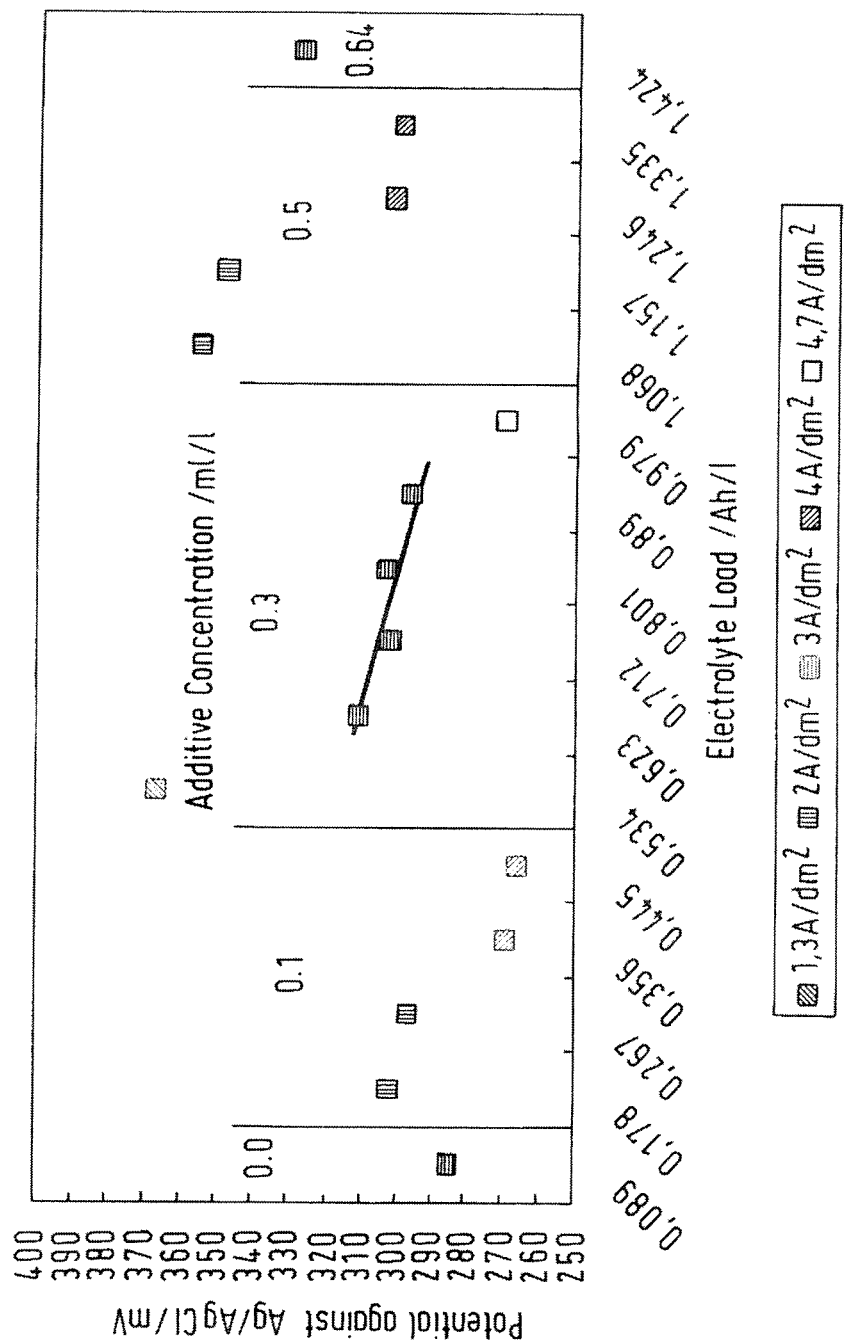
Figure 5:
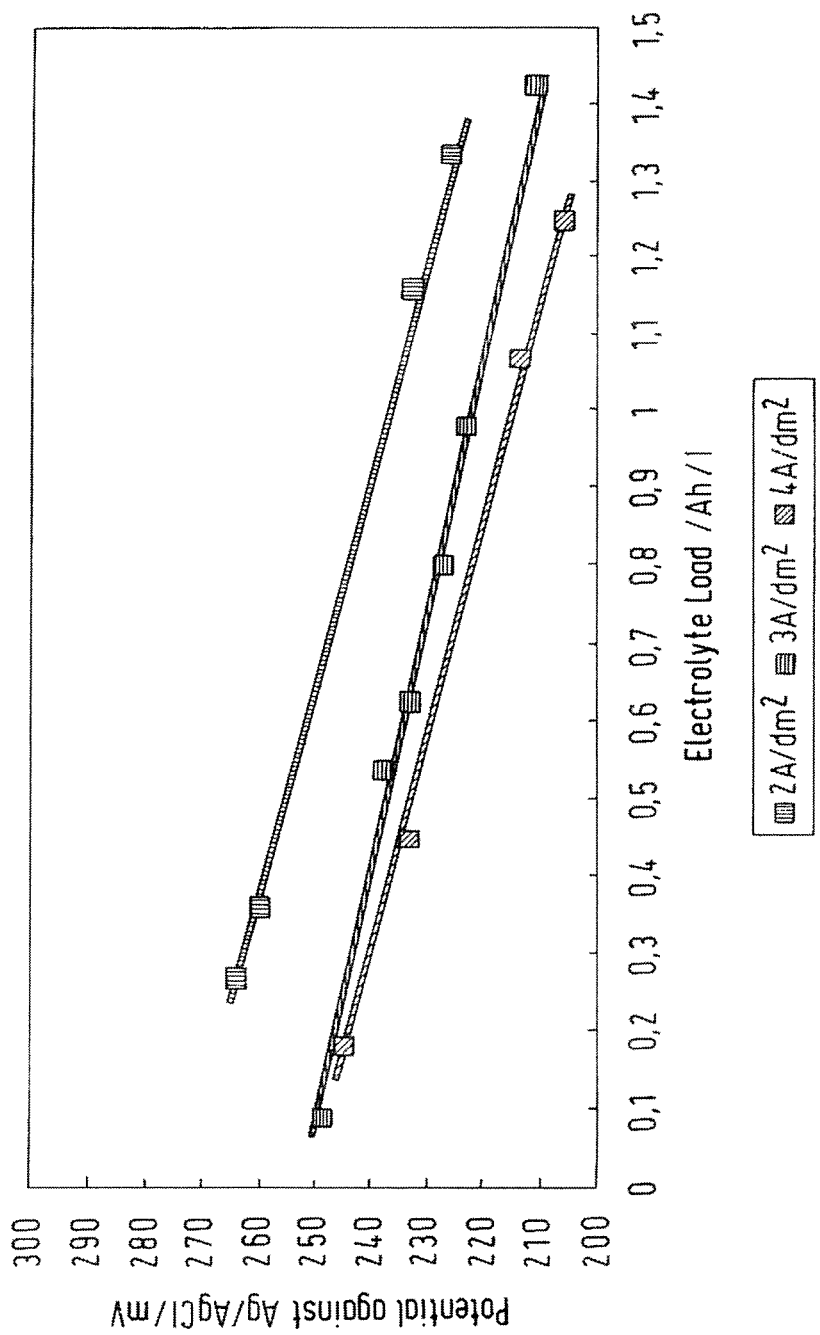

The examples described hereinafter serve to illustrate the invention. The Figs. illustrating the examples more specifically show:

FIG. 1: a schematic illustration of a measurement arrangement with a measurement cell for determining the time response of the dissolution potential;

FIG. 2: typical curves of potential transients of a bright nickel coating and of a semi-gloss nickel coating;

FIG. 3: a schematic illustration of a measurement arrangement with a measurement cell for online monitoring of nickel production baths;

FIG. 4: the dissolution potential after a change in the electrolyte load, the additive concentration and the current density during deposition of a semi-gloss nickel coating;

FIG. 5: the dependency of the dissolution potential as a function of the electrolyte load at different current densities for a bright nickel deposition electrolyte.

In the Figs., like numerals are used to denote like elements.

EXAMPLE 1

The measurement arrangement schematically shown in FIG. 1 comprises a measurement cell 1 in which there are located three electrodes: a working electrode 2, a counter electrode 3 and a reference electrode 4. The working electrode 1 is a rotating platinum electrode. The counter electrode 3 is a platinum wire and the reference electrode 4 is a silver wire that is coated with a silver chloride coating. The rotating platinum electrode 2 consists of a cylinder made from Teflon® (DuPont de Nemours), in the end side of which there is embedded a platinum disc of 0.071 $cm^2$ in size. The cylinder rotates about its axis at 500 rpm. As a result, electrolyte contained in the measurement cell is circulated in a continuous flow to the surface of the platinum disc so that constant hydrodynamic conditions prevail at the platinum surface. The electrodes 2, 3, 4 are connected to a galvanostatic current source (galvanostat) 5. Thanks to the galvanostat 5, the current flowing between the platinum electrode 2 and the counter electrode 3 is constant (e.g. 26 $A/dm^2$ or a selectable current ranging for example from >0 through 50 $A/dm^2$). Moreover, the voltage between the platinum electrode 2 and the reference electrode 4 is measured at high impedance. The reference electrode 4 is placed in proximity to the platinum electrode 2 in order to largely exclude influences from the electrolyte resistance. The galvanostat 5 in turn is connected to a computer 6 by means of which the potential of the working electrode 2 relative to the reference electrode 4 and the current between the working electrode 2 and the counter electrode 3 can be recorded and stored as well as set.

An electrolyte is given into the measurement cell 1. In the illustration shown in FIG. 1, the electrolyte can be caused to flow into the measurement cell 1 through a first connecting tubing 7 and out of the measurement cell 1 through a second connecting tubing 8.

To carry out the inspection, the platinum electrode 2 is cleaned prior to the actual measurement. Next, a diluted sulphuric acid solution (0.5 M $H_2SO_4$) is introduced into the measurement cell 1 in order to condition the platinum electrode 2. For this purpose, the potential of the platinum electrode 2 is cyclically varied, linear with time, relative to the reference electrode 4 in a potential range from −0.2 V through 1.2 V. This cycle may be run several times.

Next, the sulphuric acid is removed from the measurement cell 1 and the measurement cell 1 is rinsed with deionized water.

After this, the actual measurement is started: For this purpose, an electrolyte for depositing bright nickel is transferred into the measurement cell 1. The bright nickel electrolyte has the following basic composition: 60 g/l $NiCl_2.6H_2O$, 270 g/l $NiSO_4.6H_2O$, 45 g/l $H_3BO_3$. As an additive that determines the corrosion behaviour of the deposited coating of bright nickel, the deposition electrolyte contains a mixture of compounds containing sulphur. A current density of 3 $A/dm^2$ for example is set in order to deposit a bright nickel coating. The temperature of the electrolyte is 55° C. This is the reason why the measurement cell was heated during deposition. The thickness of the deposited coating is about 4 μm.

Upon completion of the deposition, the deposition electrolyte is removed again from the measurement cell 1. Next, the measurement cell 1 is rinsed with deionized water.

After that, a dissolution electrolyte is introduced into the measurement cell 1. The dissolution electrolyte has the following composition: 300 g/l $NiCl_2.6H_2O$, 50 g/l NaCl, 25 g/l $H_3BO_3$. The dissolution process is performed at ambient temperature. Through anodic polarization of the platinum electrode 2 and through setting a constant current between the platinum electrode 2 and the counter electrode 3, the deposited bright nickel coating is deplated successively. The potential establishing at the platinum electrode 2 relative to the reference electrode 4 is recorded depending on time (graph embedded in FIG. 1): At the beginning of dissolution, the potential measured at the platinum electrode 2 is substantially constant. As soon as the entire nickel coating has been deplated, the potential increases in leaps and bounds since water is then decomposed at the platinum electrode 2. The water decomposition takes place at a voltage that is more positive than the nickel dissolution.

After performing this measurement, the dissolution electrolyte is again removed from the measurement cell 1 and the measurement cell 1 is rinsed with deionized water.

Next, another measurement such as an inspection of a semi-gloss nickel electrolyte can be carried out. For this purpose, the platinum electrode is at first conditioned as described herein above. Next, the measurement cell is rinsed and then deposition electrolyte is introduced into the measurement cell 1. After deposition of a semi-gloss nickel coating the measurement cell 1 is rinsed again and the deposited nickel is anodically stripped from the platinum electrode.

Typical curves of the potential transients of bright nickel and semi-gloss nickel coatings are shown in FIG. 2. The bright nickel coating has been deposited in the measurement cell 1 on the platinum electrode 2 as indicated before. The semi-gloss nickel coating has been deposited on the platinum electrode 2 in the measurement cell 1 from a deposition electrolyte having the following basic composition: 60 g/l $NiCl_2.6H_2O$, 270 g/l $NiSO_4.6H_2O$, 45 g/l $H_3BO_3$. As an additive determining the corrosion behaviour of the deposited semi-gloss nickel coating, the deposition electrolyte contained a mixture of formaldehyde and of chloral hydrate. The deposition was carried out at 55° C. and at a current density of 3 $A/dm^2$.

The continuous curve represents the chronological history of the dissolution of a bright nickel coating at a current density of 26 $A/dm^2$ at room temperature and at 500 rpm. The discontinuous curve reproduces the chronology of the dissolution of a semi-gloss nickel coating under the same conditions.

It appears that in both curves one first obtained a potential plateau 10 at a low voltage against Ag/AgCl. After about 40 s, the curves leapt from the low potential values to high potential values 20, which correspond to the water decomposition at the platinum electrode.

To evaluate the two curves, one first fixes a time slot 15 in which the respective potential values were averaged. This time slot ranged from 10 s to 30 s after the deposition begun and was chosen to be the same for both dissolution procedures. Within this time slot measurement values for the dissolution potential were recorded and stored in short time intervals, for example in 0.1 s intervals. The stored values were then averaged and the averaged values for each curve were stored separately.

For the bright nickel coating, an average dissolution potential of 214 mV against Ag/AgCl was determined and for the semi-gloss nickel coating an average dissolution potential of 356 mV against Ag/AgCl was determined. A difference between the dissolution potentials of these two coatings of about 140 mV against Ag/AgCl can be calculated. This difference value corresponds to the result that would be obtained with a STEP test.

EXAMPLE 2

In another test design, the bright nickel coating and the semi-gloss nickel coating were deposited under different conditions and the thus obtained values for the dissolution potential after calculating the difference between the corresponding combinations of bright nickel coatings and semi-gloss nickel coatings were compared with values determined accordingly with the STEP test. The conditions for depositing the bright nickel coatings and the semi-gloss nickel coatings corresponded to those that had already been chosen in Example 1 if no other conditions are indicated herein after. The current density during deposition of the nickel coatings as well as the concentration of the additive determining the corrosion behaviour in the semi-gloss nickel were respectively varied. Tab. 1 compares the results of these tests against each other.

The difference values obtained with the method of the invention roughly coincide with the values obtained with the STEP test. Principally, it is to be noted that the potential difference obtained was the bigger, the higher the concentration of the semi-gloss nickel additive, the smaller the current density during deposition of the semi-gloss nickel coating and the higher the current density during deposition of the bright nickel coating. By comparing the Tests No. 7 and 9 in which the same parameter values were respectively used, it can further be shown that the reproducibility of the results for the difference of the potential values is significantly better using the method of the invention than when using the STEP test.

FIG. 3 shows a schematic illustration of a measurement arrangement that can be utilized for online monitoring production baths for nickel deposition.

The measurement cell 1 is connected to a bright nickel production bath 210 or to a semi-gloss nickel production bath 220 through a feed pipe 110 and a return pipe 120. Parts to be produced are caused to pass through the baths in the direction indicated by the arrow 200 and are nickel-plated therein. These two baths can be alternatively connected to the measurement cell 1. Deposition electrolyte can be caused to flow from the bath respectively desired into the measurement cell 1 through valves 310, 320.

Moreover, reservoirs for dissolution electrolyte 410, diluted sulphuric acid for conditioning the platinum electrode 420 and deionized water 430 are connected to the measurement cell 1 through a manifold valve 330. An additional waste container 440 is connected to the measurement cell 1 through valve 320. The respective solutions are transferred at need into the measurement cell 1 and are caused to flow into the waste container 440 after use.

EXAMPLE 3

In another test, the influence of the electrolyte load, of the concentration of the semi-gloss nickel additive and of the current density during deposition of a semi-gloss nickel coating on the dissolution potential was examined. The electrolyte load is the charge imposed in the deposition electrolyte in the tank (15 l volume) to deposit semi-gloss nickel per volume unit, expressed in [A·h/l]. For this purpose, copper sheets were coated with semi-gloss nickel at different current densities (see Table 1). The dissolution potential was measured like in the Examples 1 and 2 with a current density of 26 A/dm$^2$ on a platinum electrode rotating at 500 rpm. The potential was averaged as shown in Example 1.

For this purpose, a semi-gloss nickel electrolyte having a composition like in Example 1 was prepared in a bath tank holding 15 l. The additive was the same as described in Example 2. The additive concentration was at first 0 ml/l. Each rise in the additive concentration was added in doses in the deposition electrolyte according to the additive amounts needed to maintain the respective concentration as a function of the respective electrolyte load.

After having shortly worked in the deposition electrolyte (0.089 A·h/l), a semi-gloss nickel coating was deposited onto the rotating platinum electrode at a current density of 3 A/dm$^2$. The dissolution potential was 285 mV against Ag/AgCl. Next, semi-gloss nickel additive was added so that its concentration was 0.1 ml/l. The other tests were carried out, depositing semi-gloss nickel onto the platinum electrode at a current density of 2 A/dm$^2$ and 4 A/dm$^2$. The associated dissolution potentials were 303 mV (0.178 A·h/l) and 298 mV (0.267 A·h/l) (respectively 2 A/dm$^2$) or 270 mV (0.356 A·h/l) and 267 mV (0.445 A h/l) (respectively 4 A/dm$^2$), each against Ag/AgCl. Next, the additive concentration was increased to 0.3 ml/l. At this concentration, semi-gloss nickel was deposited at a current density of 3 A/dm$^2$ and 4.7 A/dm$^2$. The dissolution potentials were 310 mV (0.623 A·h/l), 301 mV (0.712 A·h/l), 302 mV (0.801 A·h/l), 296 mV (0.89 A h/l) (respectively 3 A/dm$^2$) or 270 mV (0.979 A h/l) (4.7 A/dm$^2$), each against Ag/AgCl. Next, the concentration of the additive was increased to 0.5 ml/l. At this concentration, semi-gloss nickel was deposited at a current density of 2 A/dm$^2$ and 4 A/dm$^2$. The dissolution potentials were 356 mV (1.068 A·h/l), 349 mV (1.157 A h/l) (respectively 2 A/dm$^2$) or 300 mV (1.246 A h/l), 299 mV (1.335 A·h/l) (respectively 4 A/dm$^2$), each against Ag/AgCl. Finally, the additive concentration was increased to a value of 0.64 ml/l. Under these conditions, semi-gloss nickel was deposited at a current density of 3 A/dm$^2$. The dissolution potential was 330 mV against Ag/AgCl. At this moment in time, the electrolyte load was 1.424 A·h/l.

The following may be inferred from this test: As shown in Example 2, the dissolution potential significantly depends on the deposition conditions, in particular on the current density during deposition. Moreover, the composition of the deposition electrolyte also has a major impact on the dissolution potential, in particular the semi-gloss nickel additive: By continuously charging the deposition electrolyte with parts that are coated in the bath, the electrolyte load increases permanently. Since the additives contained in the deposition electrolyte are consumed during deposition, such as by incorporating into the semi-gloss nickel coating, the concentration thereof continuously drops due to the treatment. Accordingly, the dissolution potential also decreased steadily while the method of the invention was being carried out, whilst the deposition conditions remained the same. When the additive concentration rose, the respective dissolution potential could be raised. It was the smaller the higher the current density used for depositing the semi-gloss nickel coating on the platinum electrode.

EXAMPLE 4

In another test, the dependence of the dissolution potential on the electrolyte load and on the current density was analyzed. For this purpose, the conditions were chosen to be the same as those described in Example 3.

The graphs shown in FIG. 5 illustrate clearly the largely linear dependence of the dissolution potential on the electrolyte load. Moreover, this also confirms that the dissolution potential is the higher the lower the current density used for depositing bright nickel onto the platinum electrode.

Accordingly, it appears, and this is impressive, that the measurement of the dissolution potential can be utilized readily not only to determine the potential difference between a bright nickel coating and a semi-gloss nickel coating in order to verify the corrosion resistance of this coating system, but that it is also indicative of the monitoring of a semi-gloss nickel electrolyte for deposition. The same applies for monitoring a bright nickel electrolyte. The possibility of monitoring the deposition electrolytes via the dissolution potential is particularly significant because it does not only permit to determine the concentration of the additive used for deposition in the analytic sense, but also to determine quantitatively its functional effect as the behaviour determining the corrosion protection behaviour of the deposited nickel coating.

It is understood that the examples and embodiments described herein are for illustrative purpose only and that various modifications and changes in light thereof as well as combinations of features described in this application will be suggested to persons skilled in the art and are to be included within the spirit and purview of the described invention and within the scope of the appended claims. All publications, patents and patent applications cited herein are hereby incorporated by reference.

TABLE 1

Comparison of potential difference values obtained with the method of the invention with results obtained with the STEP-Test

| Test No. | Current Density bright nickel [A/dm$^2$] | Current Density semi-gloss nickel [A/dm$^2$] | semi-gloss nickel additive [ml/l] | Potential-difference value [mV] | STEP-Test-Potential-difference [mV] |
|---|---|---|---|---|---|
| 1 | 3 | 3 | 0 | 37 | 0 |
| 2 | 4 | 2 | 0.1 | 58 | 26 |
| 3 | 2 | 2 | 0.1 | 33 | 27 |
| 4 | 2 | 4 | 0.1 | 9 | 0 |
| 5 | 4 | 4 | 0.1 | 33 | 22 |
| 6 | 3 | 1.3 | 0.3 | 129 | 109 |
| 7 | 3 | 3 | 0.3 | 78 | 65 |
| 8 | 1.3 | 3 | 0.3 | 38 | 64 |
| 9 | 3 | 3 | 0.3 | 76 | 61 |
| 10 | 4.7 | 3 | 0.3 | 83 | 90 |
| 11 | 3 | 4.7 | 0.3 | 47 | 55 |
| 12 | 4 | 2 | 0.5 | 142 | 133 |
| 13 | 2 | 2 | 0.5 | 116 | 110 |
| 14 | 4 | 4 | 0.5 | 96 | 88 |
| 15 | 2 | 4 | 0.5 | 74 | 83 |
| 16 | 3 | 3 | 0.64 | 117 | 101 |

The invention claimed is:

1. A method of analytically monitoring a deposition electrolyte serving for depositing a metal coating, comprising the steps of:
   a) depositing the metal coating from the deposition electrolyte onto a working electrode;
   b) electrolytically dissolving the metal coating through anodic polarisation of the working electrode with respect to a counter electrode, which is in electrolytic contact with the working electrode;
   c) recording an electrical dissolution potential at the working electrode over time, said potential occurring during dissolution of the metal coating;
   d) determining a time-averaged value of the dissolution potential;
   e) determining a difference between the time-averaged value of the dissolution potential and a reference value; and
   f) allocating said difference to a difference between the concentration of a component of the deposition electrolyte determining the dissolution potential and a reference concentration.

2. The method of analytically monitoring a deposition electrolyte as set forth in claim 1, wherein the metal coating is a constituent part of a multilayered metal coating system.

3. The method of analytically monitoring a deposition electrolyte as set forth in any one of the previous claims 1-2, wherein, prior to performing method step b), the method further comprises:
   b1) transferring the working electrode provided with the metal coating into an electrolysis cell containing a dissolution electrolyte and comprising the counter electrode.

4. The method of analytically monitoring a deposition electrolyte as set forth in claim 3, wherein the dissolution electrolyte contains ions of the metal to be deposited as well as at least one acid.

5. The method of analytically monitoring a deposition electrolyte as set forth in any one of the previous claims 1-2, wherein the electrolytic dissolution of the metal coating takes place under galvanostatic conditions.

6. The method of analytically monitoring a deposition electrolyte as set forth in any one of the previous claims 1-2, wherein the working electrode is a rotating platinum electrode.

7. The method of analytically monitoring a deposition electrolyte as set forth in any one of the previous claims 1-2, wherein the metal coating is an electrolytically deposited nickel coating.

8. The method of analytically monitoring a deposition electrolyte as set forth in any one of the previous claims 1-2, wherein the metal coating is an electrolytically deposited semi-gloss nickel coating or an electrolytically deposited bright nickel coating.

9. The method of analytically monitoring a deposition electrolyte as set forth in any one of the previous claims 1-2, wherein values of the dissolution potential at the working electrode are determined within an imposed time interval and that the values obtained are averaged in order to determine the time-averaged value of the dissolution potential.

10. The method of analytically monitoring a deposition electrolyte as set forth in any one of the previous claims 1-2, wherein the deposition electrolyte originates from a coating tank and is transferred continuously to the working electrode.

* * * * *